(12) United States Patent
Nagaoka et al.

(10) Patent No.: US 7,937,990 B2
(45) Date of Patent: May 10, 2011

(54) LIQUID CHROMATOGRAPH AND SEPARATION COLUMN

(75) Inventors: Yoshihiro Nagaoka, Ishioka (JP); Masahito Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 480 days.

(21) Appl. No.: 12/037,515

(22) Filed: Feb. 26, 2008

(65) Prior Publication Data

US 2008/0202218 A1    Aug. 28, 2008

(30) Foreign Application Priority Data

Feb. 28, 2007   (JP) .................. 2007-049928

(51) Int. Cl.
*G01N 30/50*   (2006.01)
*G01N 30/60*   (2006.01)
*B01D 15/08*   (2006.01)

(52) U.S. Cl. .............. 73/61.53; 73/61.55; 73/61.56; 210/198.2

(58) Field of Classification Search ............ 73/61.52, 73/61.53, 61.55, 61.56, 61.58; 210/198.2
See application file for complete search history.

(56) References Cited

U.S. PATENT DOCUMENTS

| | | | | |
|---|---|---|---|---|
| 3,180,825 A * | 4/1965 | Baldwin et al. | ............... | 210/678 |
| 3,855,130 A * | 12/1974 | Randau et al. | ............. | 210/198.2 |
| 4,093,550 A * | 6/1978 | Stahl et al. | ................. | 210/198.2 |
| 4,187,177 A * | 2/1980 | Stahl | ......................... | 210/198.2 |
| 4,250,035 A * | 2/1981 | McDonald et al. | ........ | 210/198.2 |
| 5,601,708 A * | 2/1997 | Leavesley | .................. | 210/198.2 |
| 6,238,565 B1 * | 5/2001 | Hatch | ........................... | 210/635 |
| 2002/0166816 A1 * | 11/2002 | Allen et al. | .................... | 210/656 |

FOREIGN PATENT DOCUMENTS

JP       11-064314       3/1999

* cited by examiner

*Primary Examiner* — Daniel S Larkin
(74) *Attorney, Agent, or Firm* — Mattingly & Malur, PC (57) ABSTRACT

A separation column and a liquid chromatograph using the separation column, which are capable of carrying out a high-speed analysis under high pressure and without a reduction in separation performance of the separation column. In the separation column, a sample and a mobile phase are introduced into a packing material. The chromatograph has a covering member for covering an outer surface of the packing material and a supporting member having the packing material covered with the covering member inserted therein, wherein the level of pressure generated within a gap located between the covering member and the supporting member on the outflow side of the gap, where the fluid-flows out of the gap, is lower than that of pressure generated within the gap on the inflow side of the gap, where the fluid is introduced.

10 Claims, 5 Drawing Sheets

LIQUID CHROMATOGRAPH AND SEPARATION COLUMN

BACKGROUND OF THE INVENTION

1. Field of the Invention

The present invention relates to a separation column for separating into components a liquid sample, which is used in a high performance liquid chromatograph (HPLC) and the like, and to a liquid chromatograph using the separation column. The invention relates more particularly to a liquid chromatograph suitable for reducing a time for analysis.

2. Description of the Related Art

A conventional high performance liquid chromatograph or the like includes a monolithic column having a structure in which a three-dimensional network skeleton and pores (a flow path, macro pore, and through pore) located in the skeleton are interconnected, the monolithic column being different from a particle-packed column used in general. The interconnected structure of the monolithic column makes it possible to increase the total surface area of the pores and possess large porosity without increasing resistance of the flow of a sample. Such a type of high performance liquid chromatograph includes a monolithic silica column having a porous material (for example, a monolithic rod or a monolithic silica rod) inserted in a fine tube to obtain high performance of the monolithic column.

It is difficult to form a porous material with a high-precision outer diameter and a high-precision curved portion, the porous material being used as a packing material. In addition, a gap may be formed between the fine tube and the porous material. To prevent a mobile phase from being leaked from a side face of the column, another column has been proposed, in which a porous material has an outer surface covered by a resin covering member, which is covered by a polyetheretherketone (PEEK) material (refer to, for example, JP-A-11-64314).

SUMMARY OF THE INVENTION

The abovementioned conventional technique is suitable for the case where the level of pressure generated within the column is about 20 to 30 MPa (Mega Pascal), which is higher than that of a sample within the conventional particle-packed column. When the level of the pressure generated within the column is set to about 50 to 100 MPa, which is necessary for high-speed analysis, a force directed toward the inside or outside of the column may be applied to the resin covering member adhering to the porous material to transform the resin covering member, or the column may be broken, due to the internal pressure of the mobile phase passing through the inside of the porous material, especially due to the case where the level of the pressure of the mobile phase is high on the side where the mobile phase is introduced and low on the side where the mobile phase is discharged. This may result in a reduction in separation performance of the column.

It is, therefore, an object of the present invention to provide a separation column and a liquid chromatograph using the separation column, which are capable of carrying out a high-speed analysis under high pressure and without a reduction in separation performance of the separation column.

To accomplish the abovementioned object, the present invention provides a liquid chromatograph having a separation column in which a sample and a mobile phase are introduced into a packing material for chromatographic separation. The liquid chromatograph also includes: a covering member for covering an outer surface of the packing material; and a supporting member with the packing material inserted therein. The liquid chromatograph is constructed so that the level of pressure of a fluid introduced between the covering member and the supporting member on the outflow side where the fluid flows out of a space located between the covering member and the supporting member is lower than that of pressure of the fluid introduced between them on the inflow side where the fluid is introduced to the space.

The separation column according to the present invention, in which a sample and a mobile phase are introduced into a packing material for chromatographic separation, includes: a covering member for covering an outer surface of the packing material; and a supporting member with the packing material inserted therein. The separation column is constructed so that the level of pressure of a fluid introduced between the covering member and the supporting member on the outflow side where the fluid flows out of the space is lower than that of the pressure of the fluid introduced between them on the inflow side where the fluid is introduced to the space.

According to the present invention, the outer surface of the packing material for chromatographic separation is covered by the covering member, the packing material being provided in the separation column. The level of the pressure of the fluid introduced between the covering member and the supporting member on the outflow side where the fluid flows out of the space is lower than the level of the pressure of the fluid introduced between them on the inflow side where the fluid is introduced to the space. The present invention makes it possible to generate pressure outside the packing material and reduce a stress applied to the covering member and a porous material, the pressure corresponding to a distribution of pressure of the mobile phase in a direction of the flow of the mobile phase in the packing material. The liquid chromatograph according to the present invention is capable of carrying out a high-speed analysis under high pressure.

DETAILED DESCRIPTION OF THE PREFERRED EMBODIMENTS

In a conventional high performance liquid chromatograph or the like, it is necessary to increase the amount of a sample transferred per unit time in order to reduce a time for analysis performed by using a particle-packed column which is used in general. To maintain the separation performance of the particle-packed column, the diameter of each of the particles to be filled needs to be reduced to increase the total area of the surfaces of the particles. Even if a particle having a diameter of about 5 µm filled in a cylindrical vessel having an inner diameter of about 4 mm, which is included in a conventional column is replaced with a particle having a diameter of about 2 μm to reduce a time for analysis to one tenth of the time, flow resistance of a sample is increased due to the reduction in the diameter of the particle. For the reason described above, it is necessary that the sample be introduced at high pressure.

Therefore, a separation column including a cylindrical porous monolithic rod is preferably used in a liquid chromatograph.

Figure 1:
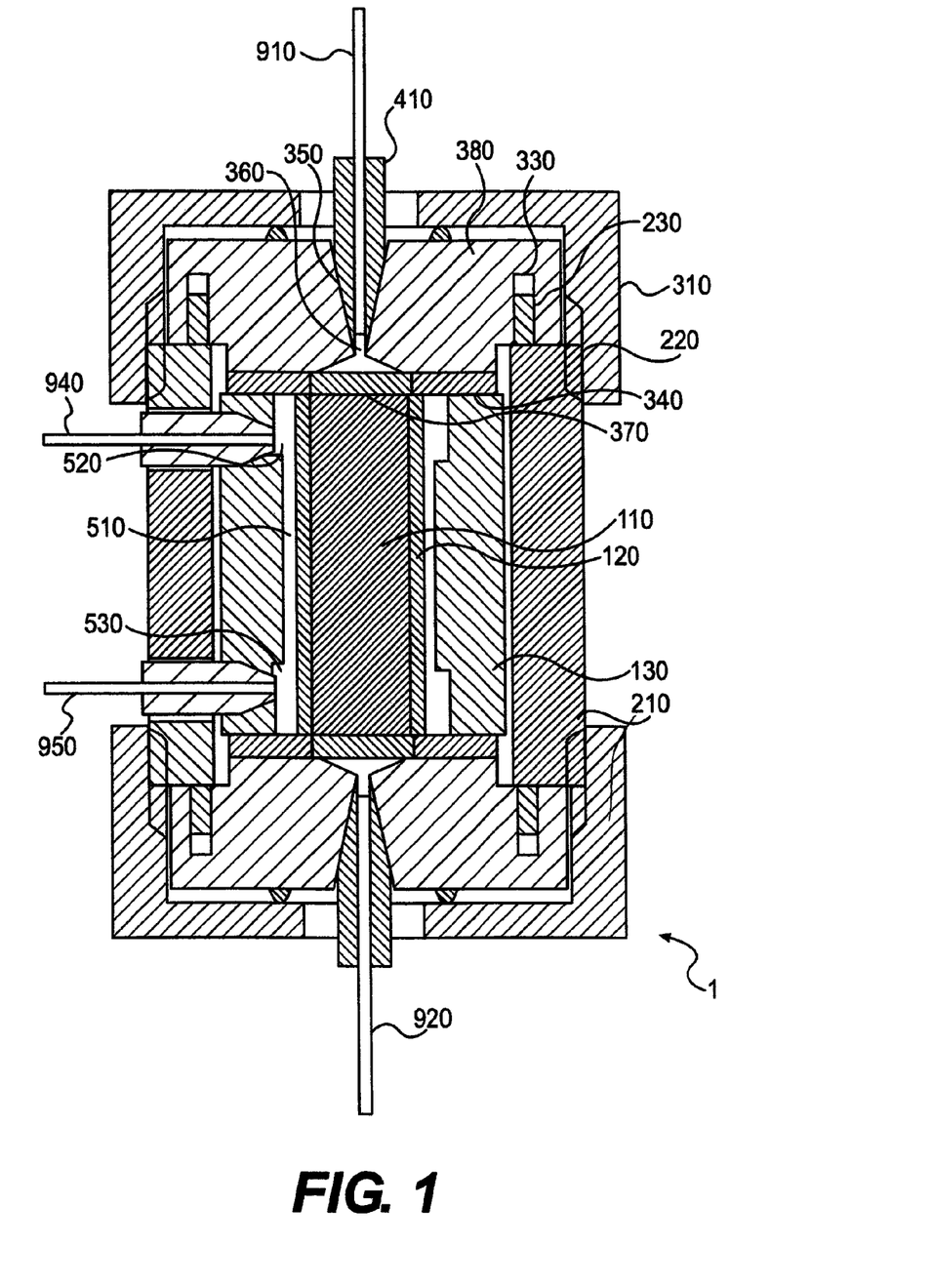
FIG. 1 is a cross sectional view of a separation column according to an embodiment of the present invention.
Figure 2:
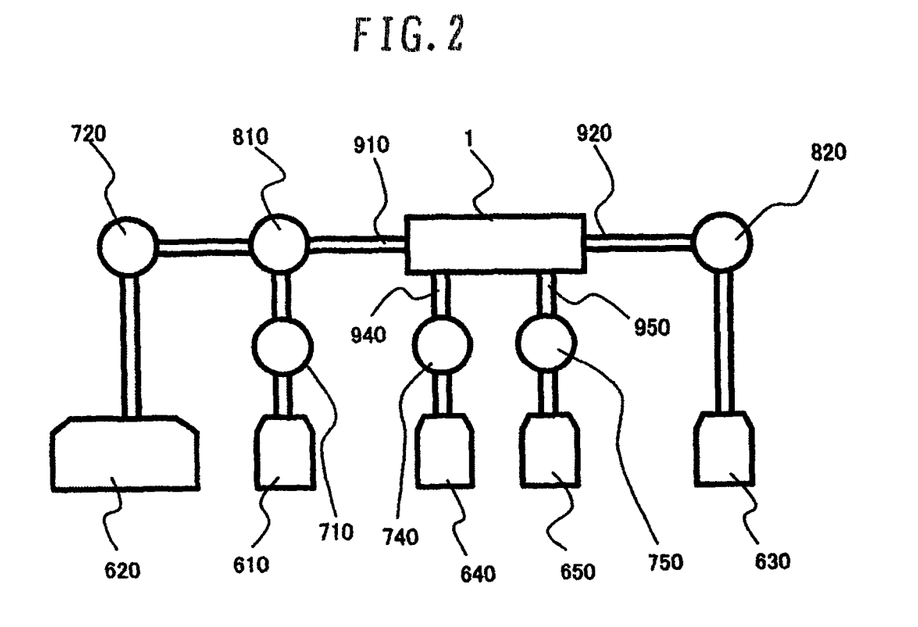
FIG. 2 is a block diagram showing a flow pipe system according to the embodiment.

FIG. 1 is a cross sectional view of a separation column according to an embodiment of the present invention. FIG. 2 is a block diagram showing a flow pipe system provided in a liquid chromatograph according to the embodiment.

In FIG. 2, a mobile phase transfer unit 710 has a pump, a valve, and a pressure indicator. The mobile phase transfer unit 710 sucks a mobile phase from a mobile phase vessel 610 and transfers the mobile phase to a sample introduction section 810. A sample transfer unit 720 sucks a sample necessary for analysis from a sample storage section 620, the sample being introduced into the mobile phase present in the sample introduction section 810. The sample storage section 620 is capable of storing a plurality of different samples. The mobile phase transfer unit 710 transfers the mobile phase with the sample introduced therein to a separation column 1 through a sample inflow pipe 910.

The separation column 1 separates the sample into chemical components based on the types of the chemical components. The chemical components flow from an outlet of the separation column 1 to a sample outflow pipe 920. The chemical components are then detected by a detector 820 which is provided on the downstream side of the separation column 1, and discharged to a sample discharge vessel 630.

Also in FIG. 2, a fluid transfer unit 740 (including a pump, a valve, and a pressure indicator) sucks a fluid used to apply pressure from a fluid vessel 640 and transfers the fluid to the separation column 1 through an inflow pipe 940. The fluid is then transferred from the separation column 1 through an outflow pipe 950 and a fluid flow rate controller 750 to a fluid discharge vessel 650.

In FIG. 1, a cylindrical porous monolithic rod (monolithic silica rod) 110 is covered with a covering member 120 and inserted in a supporting member (fine tube) 130 formed of, for example, a stainless material. A minute gap 510 is formed between the covering member 120 and the supporting member 130.

An outer holder 210 is provided on the side of the outer circumference of the supporting member 130. The outer holder 210 is fixed with a screw portion 220 by rotating a fixed member 310 with respect to the outer holder 210. A packing 340, which is provided to a connecting member 380, is thus pushed to the supporting member 130.

The connecting member 380 does not rotate even when the fixed member 310 rotates with respect to the outer holder 210 since a protruding portion 230 provided to an end portion of the outer holder 210 is positioned in a concavity 330, which is provided in the connecting member 380. That is, the packing 340 is pushed to the supporting member 130 without the rotation.

The sample inflow pipe 910 is connected to a connecting portion 350 of the connecting member 380 through a sample inflow adapter 410 so that the sample introduced to the mobile phase flows into the separation column 1. The sample then flows into a distributing member 370 through a sample inlet 360 and is distributed in a direction of the diameter of the distributing member 370. The sample then flows into the monolithic rod 110. The sample is repeatedly desorbed and moves to the outflow side where the sample flows out of the monolithic rod 110, while the sample is separated into chemical components based on the types of the chemical components in the monolithic rod 110. The chemical components then flow out of the separation column 1 to the detector 820 through the sample outflow pipe 920 and is detected by the detector 820 provided on the downstream side of the separation column 1.

The fluid, which is used to apply pressure, flows from the inflow pipe 940 to the gap 510 through an upstream spacing section 520. The fluid then flows from the gap 510 to an outflow pipe 950 through a downstream spacing section 530. The upstream spacing section 520, the gap 510 and the downstream spacing section 530 are void spaces. The void spaces and the monolithic rod 110 are substantially concentrically arranged. The gap 510 is smaller than gaps (between the covering member 120 and the supporting member 130) of the upstream spacing section 520 and the downstream spacing section 530.

The size of the gap 510 is preferably selected so that the flow resistance of the sample in the monolithic rod 110 is substantially the same as that of flow resistance of the fluid in the gap 510. That is, the area of a horizontal cross section (perpendicular to a vertical central axis of the monolithic rod 110) of the gap 510 is preferably equal to or smaller than a void portion of the monolithic rod 110 in a horizontal plane perpendicular to the vertical central axis of the monolithic rod 110. The vertical central axis of the monolithic rod 110 is substantially parallel to a straight line extending from the center of the sample inflow pipe 910 to the center of the sample outflow pipe 920.

For example, when the monolithic rod 110 has a diameter of 2 mm and a void fraction of 50%, the supporting member 130 is designed to have an inner diameter of 2.45 mm or less. When the covering member 120 has a thickness of 0.2 mm, and the monolithic rod 110 covered with the covering member 120 has a diameter of 2.4 mm, the supporting member 130 is designed to have an inner diameter of 2.79 mm or less, the diameter of the monolithic rod 110 being defined as an outer diameter of the covering member 120 in this case. Each of the above dimensions (which are the diameter of the monolithic rod 110, the inner diameter of the supporting member 130, and the thickness of the covering member 120) is measured in a direction perpendicular to the vertical central axis of the monolithic rod 110.

As described above, the flow resistance of the sample in the monolithic rod 110 can be equal to the flow resistance of the fluid in the gap 510. The distribution of the pressure generated within the monolithic rod 110 in the direction of the flow of the sample is substantially the same as the distribution of the pressure generated within the gap 510 in the direction of the flow of the fluid. Specifically, the level of the pressure within the gap 510 is decreased at a substantially constant rate from the inflow side where the fluid is introduced to the gap 510 to the outflow side where the fluid flows out of the gap 510. The pressure applied to the covering member 120 from the inside of the monolithic rod 110 is substantially equal to the pressure applied to the covering member 120 from the inside of the gap 510 at all regions of the covering member 120. Thus, the pressure applied outside the covering member 120 and the pressure applied inside the covering member 120 are substantially equal to each other even if the pressure levels are set to be high for a high-speed analysis. Therefore, the separation column is capable of preventing a gap from being formed between the monolithic rod 110 and the covering member 120 and preventing the monolithic rod 110 from being broken due to the fact that the pressure applied to the covering member 120 from the gap 510 is higher than that applied to the covering member 120 from the monolithic rod 110.

The flow resistance of the fluid in a porous material such as the monolithic rod 110 is generally larger than flow resistance of a fluid in a space formed between an inner wall of a cylindrical space and an outer wall of a cylindrical member inserted in the cylindrical space (a space formed between an inner wall of the supporting member 130 and an outer wall of the covering member 120, i.e., the gap 510). There is a possibility that the pressure generated within the monolithic rod 110 is higher than the pressure generated within the gap 510 even if the fluid flows at the same rate as the flow rate of the sample within monolithic rod 110. The flow rate of the fluid is increased by a pump included in the flow transfer unit 740 to increase the level of the pressure of the fluid within the gap 510 to the same value as the pressure generated within the monolithic rod 110, since the level of the pressure of the fluid within the gap 510 is increased in proportion with the flow rate of the fluid in the gap 510.

When the monolithic rod 110 has a high strength, the level of the pressure generated within the gap 510 is preferably higher than that of the pressure generated within the monolithic rod 110 to apply pressure to the covering member 120 from the side of the supporting member 130. When a heat shrinkable tube or the like is used as the covering member 120, a gap may be easily formed between the monolithic rod 110 and the covering member 120 since the monolithic rod 110 has an irregularity on its surface. Therefore, the pressure is applied to the covering member 120 from the side of the supporting member 130 to prevent a gap from being formed between the monolithic rod 110 and the covering member 120 and prevent a reduction in separation performance of the separation column 1.

When the detector 820 provided on the downstream side of the sample outflow pipe 920 acts as large flow resistance of the sample, the fluid flow rate controller 750 connected to the outflow pipe 950 can control the flow resistance of the fluid so that the flow resistance of the sample is substantially the same as the flow resistance of the fluid. When the detector 820 acts as small flow resistance of the sample, the fluid flow rate controller 750 is not necessary.

The fluid used to apply pressure is collected by the fluid discharge vessel 650 and reused as a fluid used to apply pressure. Alternatively, the fluid used to apply pressure may flow from the outflow pipe 950 through the fluid rate controller 750 to the fluid vessel 640.

Figure 3:
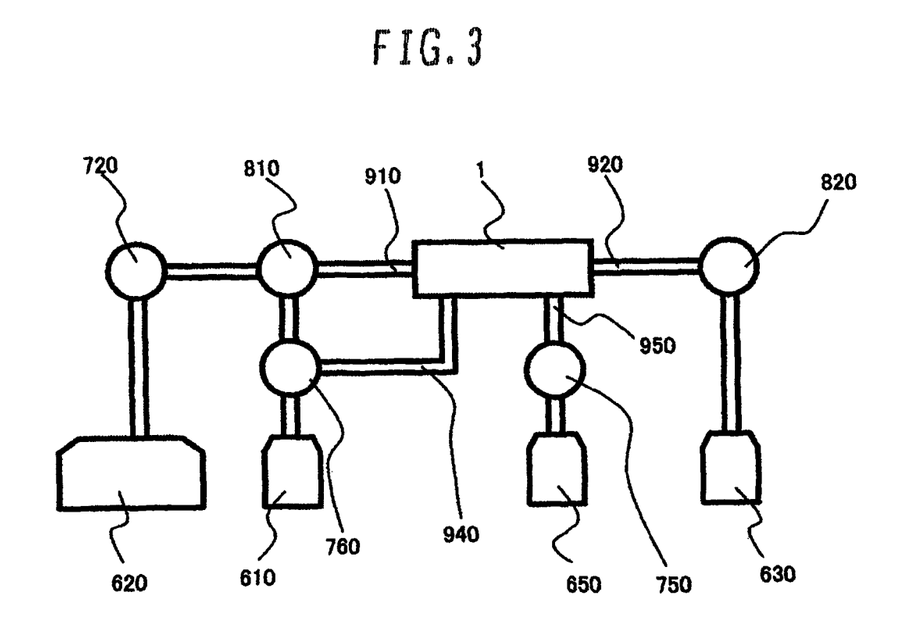
FIG. 3 is a block diagram showing a flow pipe system according to another embodiment of the present invention.

FIG. 3 shows a flow pipe system in the case where a mobile phase is used as the fluid used to apply pressure. In FIG. 3, a mobile phase transfer unit 760 sucks the mobile phase from the mobile phase vessel 610, and a flow path from the mobile phase transfer unit 760 is branched to the sample introduction section 810 and the inflow pipe 940.

The covering member 120 has an inner diameter larger than an outer diameter of the monolithic rod 110 at room temperature, the inner diameter of the covering member 120 and the outer diameter of the monolithic rod 110 being measured in a direction perpendicular to the vertical central axis of the monolithic rod 110. A heat shrinkable tube makes it easy to assemble the separation column 1 since the heat shrinkable tube is reduced in size when it is humidified. The monolithic rod 110 is preferably coated with a resin material or glass, which has fluidity, or covered with metal by evaporation. This is because the strength of the covering or of the coating is increased to improve reliability of the monolithic rod 110.

The monolithic rod 110 has an irregularity of several micrometers to several tens of micrometers on the outer surface thereof. Thus, an elastic material capable of absorbing the irregularity and being in contact with the surface of the monolithic rod 110 and a material having fluidity are suitable for the covering member 120. Since a liquid flows under high pressure in the monolithic rod 110, a material having a small thickness (which is measured in a direction perpendicular to the vertical central axis of the monolithic rod 110) or a high-modulus material is preferably used as the covering member 120 to prevent a gap from being formed by transformation of the monolithic rod 110.

Figure 4:
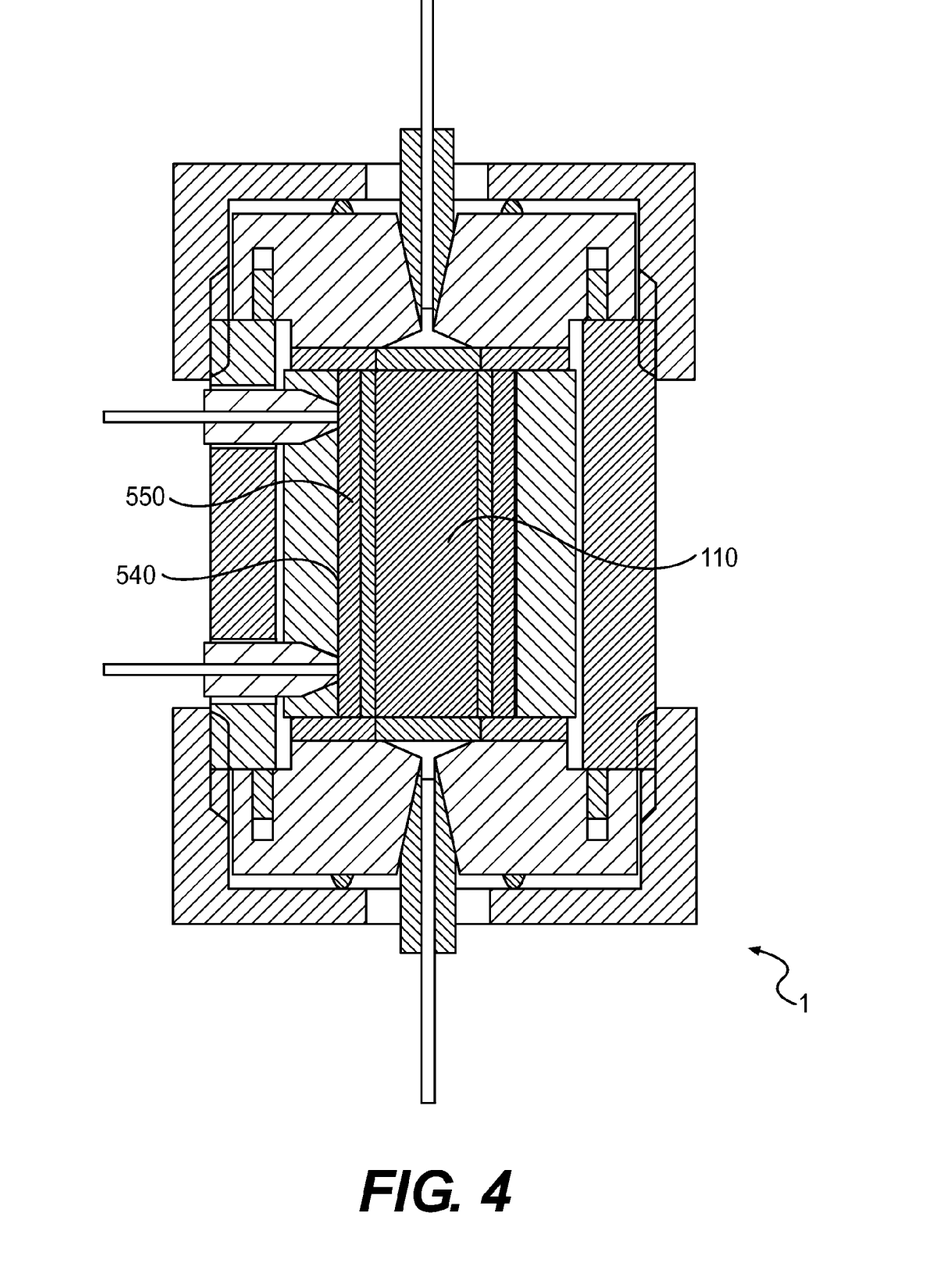
FIG. 4 is a cross sectional view of a separation column according to another embodiment of the present invention.

The gap 510 between the covering member 120 and the supporting member 130 needs to be sufficiently small so that the flow resistance of the fluid in the gap 510 is substantially equal to the flow resistance of the sample in the monolithic rod 110. However, when the monolithic rod 110 has a small diameter or has a small void fraction, the gap 510 cannot be sufficiently small. When the monolithic rod 110 has a curved portion larger than the gap 510, the monolithic rod 110 cannot be inserted into the supporting member 130. In this case, a gap 540 may be sufficiently large to fill a resistant material 550 as shown in FIG. 4.

As a material to be filled in the gap 540, a material exhibiting similar flow resistance of the fluid to that of the sample in the monolithic rod 110 may be used. For example, particles such as resin, metal or glass may be used. Alternatively, a silica gel, which is the same as the material of the monolithic rod 110, may be used. Particles of the silica gel may be filled in the gap 540 or molded within the gap 540.

The particle to be filled in the gap 540 preferably has a diameter of 1 to 10 micrometers. If the flow resistance of the fluid in the gap 540 is not equal to the flow resistance of the sample in the monolithic rod 110, the fluid transfer unit 740 controls the flow rate of the fluid. Specifically, when the flow rate of the fluid used to apply pressure is increased, the flow resistance generated by the resistant material 550 is also increased to increase the pressure of the flow of the fluid. On the other hand, when the flow rate of the fluid is decreased, the flow resistance generated by the resistant material 550 is also decreased to decrease the pressure of the flow of the fluid.

When the monolithic rod 110 has a low void fraction and high flow resistance, it is necessary that the resistant material 550 have high flow resistance. When the resistant material 550 is used, a distribution of pressure of the fluid in the resistant material 550 in a direction of a horizontal cross section of the resistant material 550 (or in a direction perpendicular to the vertical central axis of the monolithic rod 110) needs to be considered in addition to pressure applied in a direction of the vertical central axis of the monolithic rod 110 (in a direction of the flow of the mobile phase).

The level of pressure caused by the fluid flowing from the inflow pipe 940 to the resistant material 550 is reduced until the fluid reaches a point located on the side opposite to the inflow pipe 940 with respect to the vertical central axis of the monolithic rod 110 in a plane perpendicular to the vertical central axis of the monolithic rod 110. That is, the level of the pressure applied to the covering member 120 from the resistant material 550 is high on the side of the inflow pipe 940 and low on the side opposite to the inflow pipe 940 with respect to the monolithic rod 110. The level of the pressure generated within the monolithic rod 110 is substantially uniform in a plane perpendicular to the vertical central axis of the monolithic rod 110. Thus, the level of the pressure applied to the covering member 120 from the inside of the monolithic rod 110 on the side of the inflow pipe 940 is substantially equal to that of the pressure applied to the covering member 120 from the inside of the monolithic rod 110 on the side opposite to the inflow pipe 940 with respect to the monolithic rod 110 in a plane perpendicular to the vertical central axis of the monolithic rod 110. The level of the pressure applied to the covering member 120 from the inside of the monolithic rod 110 is different from that of the pressure applied to the covering member 120 from the outside of the monolithic rod 110 in a plane perpendicular to the vertical central axis of the monolithic rod 110, depending on the region of the covering member 120. The difference between the pressure levels may cause a gap to be formed between the monolithic rod 110 and the covering member 120. When the level of the pressure applied to the covering member 120 from the outside of the monolithic rod 110 is higher than that of the pressure applied to the covering member 120 from the inside of the monolithic rod 110, the monolithic rod 110 may be broken. To avoid those problems, a plurality of the inflow pipes 940 may be provided in a plane substantially perpendicular to the central axis of the monolithic rod 110 to cause the fluid to simultaneously flow from the plurality of the inflow pipes 940 to the resistant material 550, resulting in the fact that pressure levels are uniform in a plane substantially perpendicular to the central axis of the monolithic rod 110.

The level of the pressure of the fluid on the side of the outflow pipe 950 is lower than that of the pressure of the fluid on the side opposite to the outflow pipe 950 with respect to the monolithic rod 110 in a plane perpendicular to the central axis of the monolithic rod 110. To avoid the difference between the pressure levels, a plurality of the outflow pipes 950 may be provided in a plane substantially perpendicular to the central axis of the monolithic rod 110 to cause the fluid to simultaneously flow out of the resistant material 550 to the plurality of the outflow pipes 950, resulting in the fact that pressure levels are uniform in a plane substantially perpendicular to the central axis of the monolithic rod 110, similarly to the inflow pipe 940.

Figure 5:
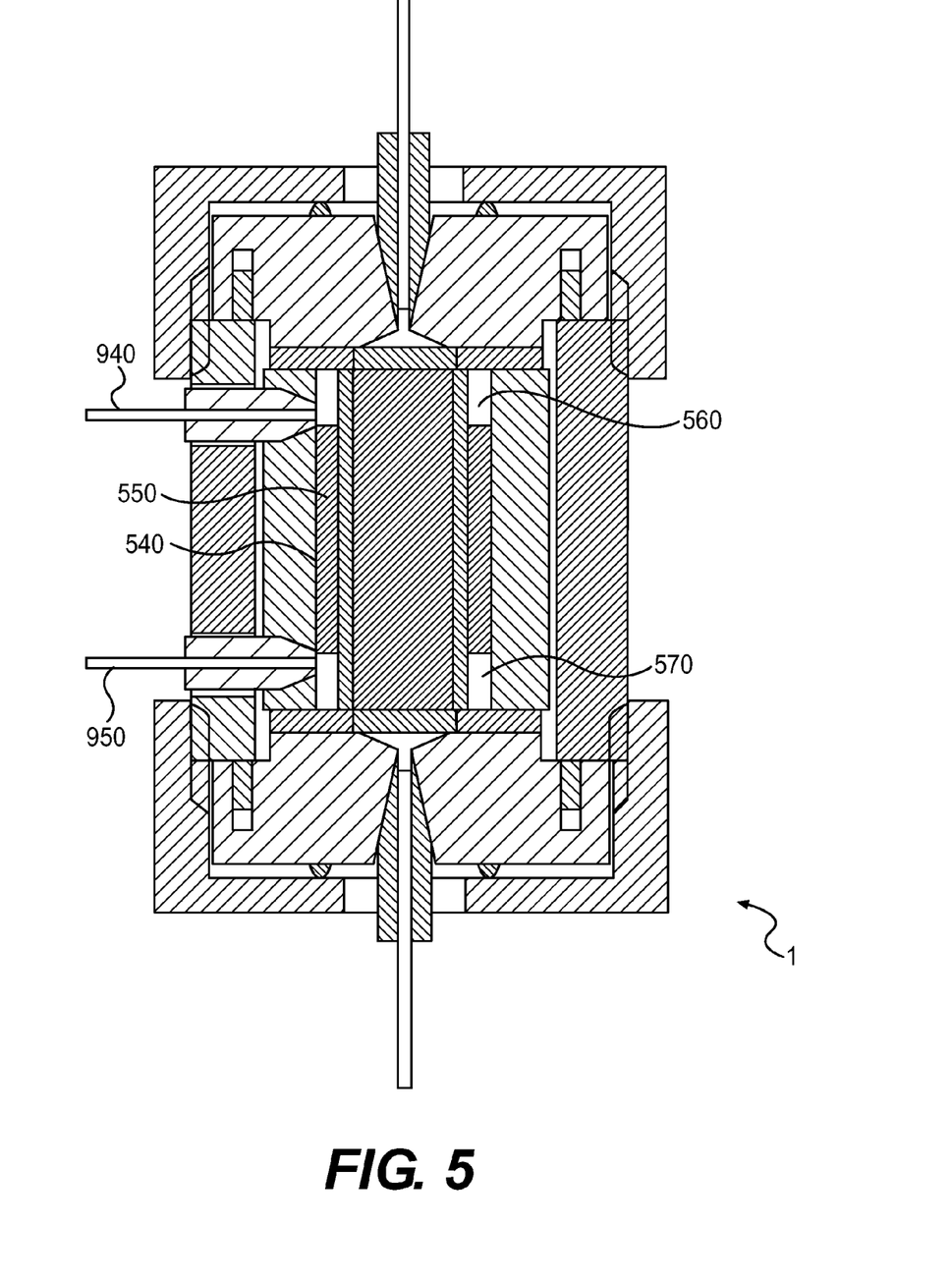
FIG. 5 is a cross sectional view of a separation column according to still another embodiment of the present invention.

FIG. 5 is a cross sectional view of the separation column in which the resistant material 550 is not filled in spaces located over and below the gap 540. The space located over the gap 540 is defined as an inflow gap 560, and the space located below the gap 540 is defined as an outflow gap 570, as shown in FIG. 5. The fluid flowing from the inflow pipe 940 to the inflow gap 560 is almost not affected by the flow resistance within the inflow gap 560. Thus, the level of the pressure of the fluid is uniform within the inflow gap 560. Similarly to the inflow gap 560, the level of the pressure of the fluid is uniform within the outflow gap 570 on the side of the outflow pipe 950. The pressure levels, therefore, are uniform within the inflow gap 560 and the outflow gap 570. When the flow resistance of the fluid is uniform within the resistant material 550, the level of the pressure of the fluid is uniform in a plane perpendicular to the central axis of the monolithic rod 110. Instead of the absences of the resistant material 550 in the inflow gap 560 and the outflow gap 570, a member having lower flow resistance than that in the resistant material 550 may be filled in the inflow gap 560 and the outflow gap 570 to obtain a similar effect to the absences of the resistant material 550.

Figure 6:
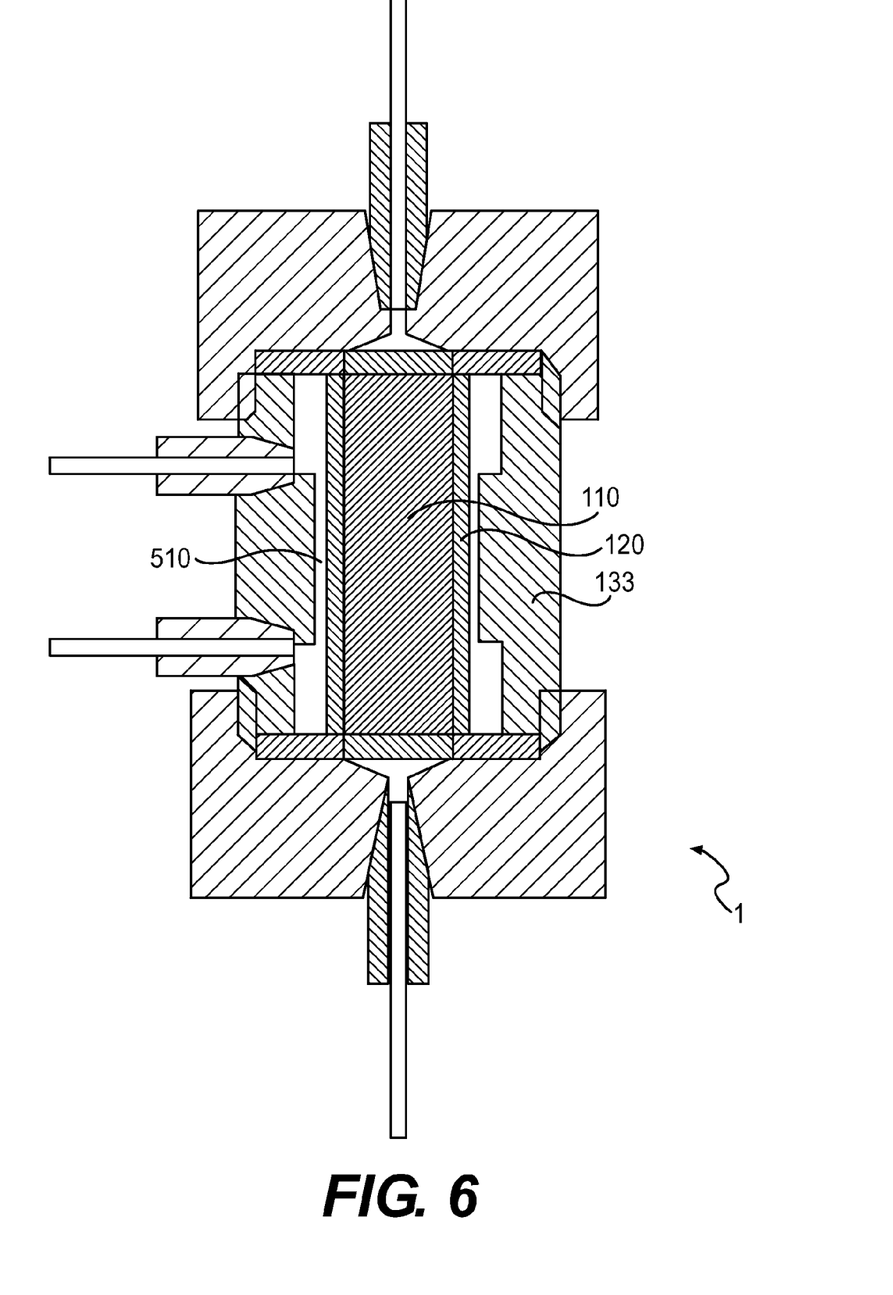
FIG. 6 is a cross sectional view of a separation column according to still another embodiment of the present invention.

As described above, the separation column 1 is provided with the outer holder 210 having the screw portion 220 and the protruding portion 230, the outer holder 210 being provided on the side of the outer circumference of the supporting member 130. If the supporting member 130 and the outer holder 210 are unified, the number of parts can be reduced. FIG. 6 is a diagram showing a separation column which is different from the separation column 1 shown in FIG. 1 in that the supporting member 130 and the outer holder 210 are unified to form a supporting member 133.

As described above with reference to FIG. 1, when the flow resistance of the sample within the monolithic rod 110 is the same as the flow resistance of the fluid within the gap 510, the distribution of the pressure generated within the monolithic rod 110 in a direction of the flow of the sample is substantially equal to the distribution of the pressure generated within the gap 510 in a direction of the flow of the fluid.

Specifically, the level of the pressure of the fluid is reduced from the inflow side where the fluid is introduced from the inflow pipe to the outflow side where the fluid flows into the outflow pipe at a substantially constant rate. Also, the level of the pressure applied to the covering member 120 from the inside of the monolithic rod 110 is substantially equal to that of the pressure applied to the covering member 120 from the gap 510 at all the regions of the covering member 120. The separation column is constructed to prevent a gap from being formed between the monolithic rod 110 and the covering member 120 and prevent the monolithic rod 110 from being broken due to the fact that the level of the pressure applied to the covering member 120 from the gap 510 is higher than that of the pressure applied to the covering member 120 from the inside of the monolithic rod 110.

The above description is made of the monolithic type separation column using the cylindrical porous monolithic rod. The present invention, however, may be applied to a particle-filled column.

Specifically, the particle-filled column may be different from the separation column 1 shown in FIG. 1 in that: a resin tube is used in place of the covering member 120; and particles are filled in the supporting member 130 in place of the monolithic rod 110.

Alternatively, the particle-filled column may be different from the separation column 1 shown in FIG. 4 in that: a resin tube is inserted in the supporting member 130 in place of the covering member 120; particles are filled in place of the monolithic rod 110; and the resistant material 550 is filled in the gap 540.

Especially, it is preferable that the level of the pressure of the fluid within the gaps 510 and 540 be higher than that of the pressure of the sample passing through the filled particles used for separation of the sample to apply pressure to the covering member 120 from the gaps 510 and 540. That is, the application of the pressure to the covering member 120 from the gaps 510 and 540 allows the covering member 120 to absorb irregularities formed by particles located on the outermost circumference of the particles, and suppresses a gap formed between the filled particles and the covering member 120. This can suppresses a reduction in the separation performance of the separation column.

What is claimed is:
1. A liquid chromatograph comprising:
   a separation column having a packing separation material into which a sample and a mobile phase are introduced, a covering member for covering an outer periphery of said packing separation material, and a supporting member into which said packing separation material covered with said covering member is inserted, a pressure between said covering material and said supporting member in a fluid outflow side being lower than a pressure between said covering material and said supporting member in a fluid inflow side;
   a sample introduction section for introducing said sample into said mobile phase;
   a mobile phase transfer unit for introducing said mobile phase and said sample into said packing separation material;
   a detector for detecting a sample separated in said packing separation material;
   a fluid transfer unit for introducing a fluid between said covering material and said supporting member;

a fluid inflow pipe for introducing a fluid between said covering member and said supporting member from said fluid transfer unit; and a fluid outflow pipe for discharging a fluid introduced between said covering member and said supporting member to an outside.

2. The liquid chromatograph according to claim 1, wherein the packing material is a cylindrical porous monolithic rod.

3. The liquid chromatograph according to claim 1, wherein the packing material is a porous monolithic rod; and which further comprises means for applying pressure corresponding to the level of pressure within the monolithic rod to a gap located between said covering member and said supporting member.

4. The liquid chromatograph according to claim 1 which further comprises a gap located between said covering member and said supporting member.

5. The liquid chromatograph according to claim 4 wherein said gap is larger at the fluid inflow side and the fluid outflow side than at a middle portion of the separation column.

6. The liquid chromatograph according to claim 5 wherein the gap at the middle portion of the separation column is filled with a resistant material and the larger portions of the gap at the fluid inflow side and the fluid outflow side are not filled with the resistant material.

7. The liquid chromatograph according to claim 4 wherein the gap is filled with a resistant material having a flow resistance similar to that of the fluid packing material.

8. A liquid chromatograph comprising:

a separation column having a packing separation material into which a sample and a mobile phase are introduced, a covering member for covering an outer periphery of said packing separation material, and a supporting member into which said packing separation material covered with said covering member is inserted, a pressure between said covering material and said supporting member in a fluid outflow side being lower than a pressure between said covering material and said supporting member in a fluid inflow side;

a sample introduction section for introducing said sample into said mobile phase;

a mobile phase transfer unit for introducing said mobile phase and said sample into said packing separation material;

a detector for detecting a sample separated in said packing separation material;

a fluid transfer unit for introducing a fluid between said covering material and said supporting member;

a mobile phase inflow pipe for introducing said mobile phase between said covering member and said supporting member from said mobile phase transfer unit, said mobile phase inflow pipe being branched from said mobile phase transfer unit; and a mobile phase outflow pipe for discharging a mobile phase introduced between said covering member and said supporting member to an outside.

9. A separation column for a liquid chromatograph said separation column comprising:

a packing separation material into which a sample and a mobile phase are introduced;

a covering member for covering an outer periphery of said packing separation material;

a supporting member into which said packing separation material covered with said covering member is inserted, a fluid inflow pipe for introducing a fluid between said covering member and said supporting member; and a fluid outflow pipe for discharging a fluid introduced between said covering member and said supporting member to an outside, wherein a pressure between said covering member and said supporting member in a fluid outflow side is smaller than a pressure between said covering member and said supporting member in a fluid inflow side.

10. The separation column according to the claim 9, wherein the packing material is a cylindrical porous monolithic rod.

\* \* \* \* \*